(12) United States Patent
Andersson et al.

(10) Patent No.: US 7,175,767 B2
(45) Date of Patent: Feb. 13, 2007

(54) PREPARATION OF A METAL CHELATING SEPARATION MEDIUM

(75) Inventors: Lars C. Andersson, Uppsala (SE); Tesfai Gebru, Uppsala (SE); Tania Ahmad, Uppsala (SE); John Clachan, Uppsala (SE); Andreas Axén, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 12 days.

(21) Appl. No.: 10/549,083

(22) PCT Filed: Apr. 1, 2004

(86) PCT No.: PCT/SE2004/000502

§ 371 (c)(1),
(2), (4) Date: Sep. 12, 2005

(87) PCT Pub. No.: WO2004/087284

PCT Pub. Date: Oct. 14, 2004

(65) Prior Publication Data

US 2006/0199950 A1    Sep. 7, 2006

(30) Foreign Application Priority Data

Apr. 4, 2003    (SE) .................................... 0301011

(51) Int. Cl.
*B01D 15/08*    (2006.01)
*B01J 20/26*    (2006.01)
*C07K 1/14*    (2006.01)

(52) U.S. Cl. .................. 210/635; 210/656; 210/198.2; 502/402; 502/439; 530/412

(58) Field of Classification Search ............... 525/54.3; 530/351, 400, 412; 556/49
See application file for complete search history.

(56) References Cited

U.S. PATENT DOCUMENTS

| 4,551,271 A | 11/1985 | Hochuli |
| 4,877,830 A | 10/1989 | Döbeli et al. |
| 5,047,513 A | 9/1991 | Döbeli et al. |

FOREIGN PATENT DOCUMENTS

WO    WO 01/81365    11/2001

*Primary Examiner*—Maryam Monshipouri
*Assistant Examiner*—Marsha Tsay
(74) *Attorney, Agent, or Firm*—Yonggang Ji (57) ABSTRACT

The present invention relates to the preparation of a metal chelating separation medium, which comprises providing a compound defined by formula: $R-O-CO-(CH_2)_n-CHNH_2-CO-OH$ wherein R is a selectively cleavable group; and n is an integer of 1–4; reacting it with ethyl alcohol; derivatisation; cleavage of R; immobilisation of the resulting compound to a base matrix; and deprotection of the carboxylic acid. In one embodiment, the compound provided in the first step is ethyl ester of aspartic acid or of glutamic acid, and the derivatisation agent is bromo-acetic acid ethyl acetate.

12 Claims, 2 Drawing Sheets

PREPARATION OF A METAL CHELATING SEPARATION MEDIUM

CROSS REFERENCE TO RELATED APPLICATIONS

This application is a filing under 35 U.S.C. § 371 and claims priority to international paten application No. PCT/SE2004/000502 filed Apr. 1, 2004, published on Oct. 14, 2004 as WO 2004/087284 and also claims priority to patent application No. 0301011-3 filed in Sweden on Apr. 4, 2003; the disclosures of which are incorporated herein by reference in their entireties.

TECHNICAL FIELD

The present invention relates to a method of preparing a separation medium, which comprises a plurality of polydentate metal chelating affinity ligands immobilised to a base matrix. The invention also encompasses a process of chromatography, wherein a so prepared separation medium is used. Finally, the invention relates to a kit, which comprises a chromatography column packed with a separation medium prepared by the method according to the invention and metal ions suitable for its use.

BACKGROUND

In any chemical or bioprocessing industry, the need to separate and purify a product from a complex mixture is a necessary and important step in the production line. Today, there exists a wide market of methods in which industry can accomplish these goals, one of which is chromatography. Chromatography is quite well suited to a variety of uses in the field of biotechnology, since it can separate complex mixtures with great precision and also is suitable for more delicate products, such as proteins, since the conditions under which it is performed are not typically severe.

One chromatography method, which is an especially sensitive separation technique and also applicable to most types of proteins, is metal chelate affinity chromatography (MCAC), also known as immobilised metal ion adsorption chromatography (IMAC). This technique is commonly used in purification schemes together with another chromatographic step, such ion exchange chromatography (IEX) and/or hydrophobic interaction chromatography (HIC).

More specifically, IMAC utilises matrices that comprises a group capable of forming a chelate with a transition metal ion, which chelate in turn is used as the ligand in chromatography to adsorb a compound from a liquid. The binding strength in IMAC is affected predominately by the species of metal ion, the pH of the buffers and the nature of the ligand used. Since the metal ions are strongly bound to the matrix, the adsorbed protein can be eluted either by lowering the pH or by competitive elution.

In general, IMAC is useful for separation of proteins or other molecules that present an affinity for the transition metal ion of the matrix. For example, proteins will bind to the matrix upon the presence of accessible histidine, cysteine and tryptophan residues, which all exhibit affinity for the chelated metal.

With the advent of molecular biological techniques, proteins are now easily tailored or tagged with one or more histidine residues in order to increase their affinity to metal chelated ligands, and accordingly, metal chelate chromatography has more recently assumed a more important role in the purification of proteins.

Simple chelators have been suggested as ligands for IMAC, such as iminodiacetic acid (IDA). IDA, coupled to agarose supports and subsequent charged with various metals, such as $Cu^{2+}$, $Zn^{2+}$ and $Ni^{2+}$, has been used for capture of proteins and peptides and is also available as commercial resins. More specifically, U.S. Pat. No. 4,551,271 (Hochuli, Hoffmann-La Roche Inc.) discloses a metal chelate resin which comprises IDA ligands, in the purification of interferon. The best results are obtained with this resin if the interferon has already been partially purified. The resin can according to the specification be prepared in a known manner by treating agarose with epichlorohydrin or epibromohydrin, reacting the resulting epoxide with iminoacetic acid disodium salt and converting the product into the copper or zinc salt by washing with a copper (II) or zinc solution.

More recently, EP 87109892.7 (F. Hoffmann-La Roche AG) and its equivalent U.S. Pat. No. 4,877,830 (Döbeli et al, assigned to Hoffmann-La Roche Inc.) disclosed a tetradentate chelator known as nitrilotriacetic acid (NTA) for use with metals that have six coordination sites. More specifically, the matrices can be described by the general formula [Carrier matrix]-Spacer-NH—$(CH_2)_x$—CH(COOH)—N$(CH_2COO^-)_2 Ni^{2+}$, wherein x=2–4. The disclosed matrix is prepared by reacting an amino acid compound of the formula R—HN—$(CH_2)_x$—CH(NH$_2$)—COOH, wherein R is an amino protecting group and x is 2, 3 or 4, with bromoacetic acid in alkaline medium and subsequently, after an intermediate purification step, cleavage of the protecting group and reacting this group with an activated matrix, whereby an amide bond is formed. However, this procedure may involve disadvantages, since the media obtained presents the immobilised desired chelating ligand as well as some unreacted carboxylic groups, thus yielding a heterogeneous media. In addition, the efficiency of the suggested alkylation chemistry is not satisfactory, and after the deprotection step of the amine, the product is not well defined regarding rest products from neutralisation and cleavage.

Finally, WO 01/81365 (Sigma-Aldrich Co.) discloses a metal chelating composition that according to the specification is capable of forming relatively stable chelates with metal ions and exhibits an improved selectivity for polyhistidine tagged proteins. According to said WO 01/81365, the linkage between the chelator and the resin is an important parameter for the selectivity, and the linkage is a neutral ether, a thioether, a selenoether or an amide. The disclosed compositions are coupled to an insoluble carrier, such as Sepharose™ according to given examples. The chromatographic media is produced in two different ways; either by a solid phase reaction directly on to the pre-activated solid support eventually used in the chromatographic media, or by a separate in solution synthesis of the intermediate product N,N,N',N'-tetrakis(carboxymethyl)-L-cystine that is eventually coupled to the solid support.

Accordingly, there is still a need in this field of alternative methods for synthesis of IMAC ligands and immobilisation thereof to a base matrix.

SUMMARY OF THE PRESENT INVENTION

One object of the present invention is to provide a method of preparing a separation medium comprised of polydentate metal chelating affinity ligands immobilised to a base matrix, in which method a novel coupling chemistry is used. A specific object of the invention is to provide such a method, wherein a novel protection/deprotection scheme is utilised.

Another object of the invention is to provide a method of preparing a separation medium comprised of polydentate metal chelating affinity ligands immobilised to a base matrix, in which method the same kind of functionalities are used for immobilisation of the ligands and for functional groups of the ligands.

A further object of the invention is to provide a method of preparing a separation medium comprised of polydentate metal chelating affinity ligands immobilised to a base matrix, wherein the metal chelating ligands are easily immobilised to the desired level of substitution onto the base matrix.

Other objects and advantages of the present invention will appear from the detailed description that follows.

DEFINITIONS

The term "separation medium" is used herein for a material useful e.g. as packing of a chromatography column, and more specifically consists of one or more ligands coupled to a base matrix. Thus, the base matrix acts as a carrier, while the ligands provide functionalities that interact with, or bind, target substances in chromatography.

The term "spacer" is used for a chemical entity that distances a ligand from the base matrix.

The term "ligand" means herein a chemical entity capable of binding target substances. Such target substances may be one, which it is desired to isolate or remove by chromatography, or alternatively an analytical target substance. In the present context, it is understood that the term "substance" encompasses molecules as well as more complex compounds.

The term "electrophile" means an atom, molecule or chemical group that is attracted to electrons or accepts them. Thus, an electrophile is also known as an "electron-acceptor".

The term "tetradentate metal chelating" ligands refers to ligands with four donor atoms that can coordinate to, i.e. chelate, a metal simultaneously. Thus, a polydentate ligand exhibits four donor atoms and occupies two or more sites in a coordination sphere.

The term "metal chelating functionalities" refers to the groups that provide donor atoms. Usually, the functionalities are distanced from each other and hence the term "ligand arm" is sometimes used for an entity that presents a functionality.

The term "immobilisation" is used for chemical attachment i.e. binding or coupling of ligands to a base matrix.

The term "gel" is sometimes used herein for a base matrix, which is in the form of a gel.

DETAILED DESCRIPTION OF THE INVENTION

In a first aspect, the present invention relates to a method of preparing a separation medium comprised of a plurality of polydentate metal chelating affinity ligands immobilised to a base matrix, which method comprises the steps of (i) providing a compound defined be the general formula (I) below $$R-O-CO-(CH_2)_n-CHNH_2-CO-OH \qquad (I)$$

wherein
R is a selectively cleavable group; and
n is an integer of 1–4;

(ii) reacting said compound with ethyl alcohol to provide esterification of the terminal carboxylic acid;

(iii) derivatisation of the product of step (ii) by adding at least one agent comprising an electrophile attached to an ethyl-protected carboxylic acid functionality;

(iv) selective cleavage of R from the compound to provide one free carboxylic acid functionality; and (v) immobilisation of the compound that results from step (iv) to a base matrix via said free carboxylic acid functionality, after which deprotection of the remaining carboxylic acid groups is obtained by specific hydrolysis.

As the skilled person in this field will understand, the phrase "ethyl-protected carboxylic acid functionality" means a carboxylic acid protected as its ethyl ester.

Thus, the present invention provides a novel synthetic route for preparing IMAC separation media, wherein a carboxylic functionality is used for coupling ligands to the base matrix. As the skilled person in this field will realise to successfully perform such an immobilisation in a case where one carboxylic functionality is to be used for coupling while other carboxylic functionalities are to be used as IMAC ligands, protection of the ligand functionalities during the immobilisation step will be required. According to the present invention, it was unexpectedly found that to obtain a satisfactory protection, the nature of the agent used in step (ii) for esterification is critical. More specifically, the present inventor has found that use of the simplest and most straightforward option in this context, namely methyl groups, for such protection could not provide a satisfactory deprotection, while ethyl groups did. Accordingly, as appears from the above, the esterification of step (ii) uses ethyl alcohol. General conditions for the esterification, such as reaction times, amounts etc, can easily be selected by the skilled person in this field.

The nature of the selectively cleavable group R is not essential, as long as it allows selective cleavage of R without any substantial affect on the protective ethyl groups. Put differently, the cleavage of R from the compound should not be equivalent to the hydrolysis used for deprotection in step (v), as will be discussed in more detail below. Thus, in one embodiment, R is an acid-labile group, e.g. tert-butyl, or any other protecting group that can be selectively cleaved without removing the ethyl esters.

As appears from the above, the compound provided in step (i), i.e. the starting material, comprises the above-discussed carboxylic functionality, which is subsequently used for immobilisation to a base matrix; an amine that allows derivatisation according to step (iii); and an additional carboxylic functionality. Thus, depending on the nature of the re-agent used in step (iii), since each one of said carboxylic functionalities will provide ligand arms in the final structure, the present method provides tridentate or tetradentate metal chelating affinity ligands immobilised to a base matrix. As the skilled person in this field will understand, the value of n is not essential to the invention, but is rather decided by the choice of starting materials. Accordingly, in one embodiment, n is an integer of 1 or 2. In a specific embodiment, the compound defined by Formula (I) is ethyl ester of aspartic acid or of glutamic acid, which is commercially available e.g. from Bachem or easily prepared by the skilled person in this field.

Step (iii) is a derivatisation of the $NH_2$ of the compound, and accordingly the agent(s) used must comprise an electrophile capable of attacking nitrogen. In a specific embodiment, the reagent used in step (iii) is defined by the following formula (II)

$$E\text{-}(CH_2)_m\text{--}CO\text{--}O\text{--}CH_2\text{--}CH_3 \quad (II),$$

wherein E is the electrophile and m is an integer of from 0–2. As the skilled person in this field will understand, the value of m is decided by the desired length of the ligand arms. In one embodiment, m is 1.

In one embodiment, the electrophile E is selected from the group that consists of a double bond (C=C); C—Y, wherein Y represents a halogen, such as Br, I, Cl, a mesylate, or a tosylate group; and an acid or an activated acid. Such an acid or activated acid can be illustrated by WC=O, wherein W is formed from N-hydrosuccinimide, pentafluorophenol, para-nitrophenol or isopropyl chloroformate.

In the most preferred embodiment, the electrophile comprises Br, and E is C—Br. In an advantageous embodiment, Formula II defines bromo-acetic acid ethyl ester, which is commercially available e.g. from Aldrich. Methods for reacting an $NH_2$ group with a group carrying a halogen or another leaving group are well known in this field and are conveniently performed at ambient temperature in a solvent such as N,N-dimethylformamide (DMF). Further, if desired, the skilled person can easily monitor the reaction and confirm the derivatisation obtained by a conventional method such as liquid chromatography—mass spectrometry (LC-MS).

In one embodiment, the derivatisation of step (iii) is provided by adding one kind of derivatisation agent in an amount adapted to either attach one or two ligand arms to the amine, i.e. in a molar amount of either about 1:1 or about 2:1 to the compound provided in step (i). In an alternative embodiment, two derivatisation agents are used, which can be varied within the above-discussed limits. In this embodiment, the electrophilic parts of the agents are preferably of the same nature in order to facilitate the derivatisation.

In the preferred embodiment, the base matrix, to which the selectively cleaved compound obtained from step (iv) is immobilised, is comprised of essentially spherical particles known as beads. In the most preferred embodiment, the beads are porous. However, in alternative embodiments, the base matrix is a monolith, a membrane, a filter, one or more chips, surfaces, capillaries or any other suitable solid support.

In one embodiment, such suitable porous polymer beads are made from natural polymers, for example of a crosslinked carbohydrate material, such as agarose, agar, cellulose, dextran, chitosan, carrageenan, gellan, alginate etc. The beads are easily prepared by the skilled person in this field according to standard methods, such as inverse suspension gelation (S Hjertén: Biochim Biophys Acta 79(2), 393–398 (1964) or spinning disk technique (see e.g. WO 88/07414 (Prometic Biosciences Inc)). Alternatively, natural polymer beads are obtained from commercial sources, such as Amersham Biosciences AB, Uppsala, Sweden. Illustrative trade names of such useful natural polymer beads are e.g. of the kind known as Sepharose™ or Sephadex™.

In another embodiment, such suitable porous polymer beads are made from synthetic polymers, such as crosslinked synthetic polymers, e.g. styrene or styrene derivatives, divinylbenzene, acrylamides, acrylate esters, methacrylate esters, vinyl esters, vinyl amides etc. Such polymers are easily produced according to standard methods, see e.g. "Styrene based polymer supports developed by suspension polymerization" (R Arshady: Chimica e L'Industria 70(9), 70–75 (1988)). Alternatively, synthetic polymer beads are obtained as commercially available products, such as Source™ (Amersham Biosciences AB, Uppsala, Sweden).

In an illustrative embodiment, before immobilisation, the base matrix is allylated, e.g. by treatment with an epoxide carrying an allyl functionality at suitable temperatures and reaction times. One example of such a commonly used allyl-functional epoxide is allyl glycidyl ether (AGE). However, as the skilled person in this field will realise, there are many other well-known reagents that are equally useful in this context. Such allyl groups are activated by bromination or alternatively, the coupling is a free radical reaction. The free radical used can be any suitable commercially available initiator, UV etc. For a general review of immobilisation techniques useful to this end, see e.g. Immobilized Affinity Ligand Techniques, Hermanson et al, Greg T. Hermanson, A. Krishna Mallia and Paul K. Smith, Academic Press, INC, 1992.

This can be used for producing matrices that possess primary amines by reacting the activated material e.g. with ammonia or hexamethylene diamine. As mentioned above, one carboxylic functionality of the otherwise protected ligands is utilised for the immobilisation thereof to a base matrix via a reaction of said carboxylic acid with a primary amine present on the base matrix. As will be discussed in more detail below, such amines may be present or introduced on the base matrix. In an alternative embodiment, the compound obtained after step (iv) is coupled to the base matrix via a spacer, in which case amine groups are available on the spacer. Such spacers are well known in this field, and are easily selected depending on the intended use of the separation medium, especially depending on the target substances. The basic requirement of the spacer is that it exhibits a sufficient hydrolytic stability for use as separation medium under standard conditions for IMAC, and more importantly, during final deprotection of carboxylic functions. For a detailed discussion of spacers, see e.g. WO 99/65607 (Amersham Pharmacia Biotech, Uppsala, Sweden). As is well known, spacers are often introduced via the standard techniques for immobilisation.

An illustrative example of a separation medium prepared according to the present invention is defined by the following structure:

As the skilled person in this field will understand, suitable intermediate washing steps can be included between one or more of the various steps described herein.

As mentioned above, the deprotection of step (v) is performed by hydrolysis. Thus, in one embodiment, step (v) is performed by adding a base, such as is an alkali hydroxide, e.g. NaOH, or any other base that does not have any negative impact on the structure. If NaOH is used, a period of time of between about 30 minutes up to a few hours, such as three hours, can be used for deprotection. In addition, chemistries useful for protection/deprotection of functionalities are well-known in this field, and the skilled person in this field can easily deprotect the carboxylic functionalities according to standard methods.

In a second aspect, the present invention relates to a kit for preparing a separation medium comprising a plurality of tetradentate metal chelating affinity ligands immobilised to a base matrix, which kit comprises, in separate compartments: a base matrix; ethyl ester of glutamic acid; ethyl alcohol; at least one derivatisation agent, which is comprised of an electrophile attached to an ethyl-protected carboxylic acid functionality; an acid; and a base, together with written instructions for the use thereof In one embodiment, the base matrix comprises activated groups that are readily reactive with a carboxylic functionality. In an alternative embodiment, the present kit comprises all the components above except the base matrix, which is easily provided by the user. In one embodiment, the derivatisation agent is defined by formula (II) as defined above. In the most advantageous embodiment, the derivatisation agent is bromo-acetic acid ethyl ester. In a specific embodiment, the kit comprises ethyl ester of aspartic acid or of glutamic acid and the derivatisation agent in a molar ratio of about 1:2.

In a third aspect, the present invention relates to a separation medium prepared by a method as defined above. In one embodiment, the present separation medium comprises tridentate ligands. In another embodiment, the present separation medium comprises tetradentate ligands. The separation medium according to the invention can then be charged with a suitable metal ion, such as Cu(II), Zn(II), Ni(II), Ca(II), Co(II), Mg(II), Fe(III), Al(III), A(III), Sc(III) etc, and used according to well known principles of IMAC, e.g. as outlined in the section "Background" above. In the most preferred embodiment, $Ni^{2+}$ is used. The separation medium according to the invention is advantageously used in a process of chromatography, as discussed in more detail below, or for analytical purposes. In the last mentioned embodiment, target molecules are detected and/or quantified. Suitable base matrixes for analytical purposes are e.g. microtitre plates or any one of the above discussed.

The present invention also encompasses a chromatography column packed with a medium as described above. The column can be of any size, such as for large-scale production or lab-scale, or suitable for analytical purpose. The column can also be combined with separation medium and optionally liquids into a second kind of kit, which is also encompassed by the present invention. In one embodiment, such a kit according to the invention comprises metal ions, such as $Ni^{2+}$ ions.

Further, the invention also encompasses a kit for performing immobilised metal ion adsorption chromatography (IMAC), which kit comprises a chromatography column as described above, metal ions for chelate formation and written instructions for the its use. In an advantageous embodiment, the column is made from any conventional material, such as a biocompatible plastic, e.g. polypropylene, or glass. In a specific embodiment, the column is provided with luer adaptors, tubing connectors, and domed nuts. Suitable metal ions are as exemplified below in the context of the process. The kit according to the invention can be for analytical or preparative purposes.

In addition, the present invention also relates to a process of separating at least one target substance from a liquid, which process comprises to provide a separation medium as defined above, to charge said medium with suitable metal ions to form chelates and to contact said medium with the liquid to adsorb the target substance(s) thereon. In an advantageous embodiment, the process also comprises a step of eluting the target substance(s) from the separation medium by adding a liquid that desorbs the target substance(s) from the separation medium. In one embodiment, the elution is obtained by using a liquid that comprises a decreasing pH gradient or by applying a gradient giving an increasing imidazole concentration. The general principles of chromatography for separating a target substance as discussed above are well-known in this field, and the skilled person in this field can easily adopt the necessary parameters for use of the present process. (For more details regarding IMAC, see e.g. Porath, J., Carlsson, J., Olsson, I. & Belfrage, G. (1975): *Metal chelate affinity chromatography, a new approach to protein fractionation*, Nature, vol. 258, pp. 598–599; and Porath, J. (1992), Protein expression and purification, vol. 3, pp. 263–281.)

The present process can be used for separation of desired proteins and peptides that exhibit surface histidine, cysteine and tryptophane residues with an affinity for the chelated metal ions. In the most advantageous embodiment, the present process is used for recombinant proteins that comprise a number of histidine residues, such as His-tagged proteins or His fusion proteins. In one embodiment, one target substance is a membrane protein. In alternative embodiments, the present process is used for separation of other target substances that comprise phosphate groups and nitrogen atoms to which transition metal ions can coordinate, such as virus and cells, polysaccharides, oligonucleotides etc.

DETAILED DESCRIPTION OF THE DRAWINGS

Figure 1:
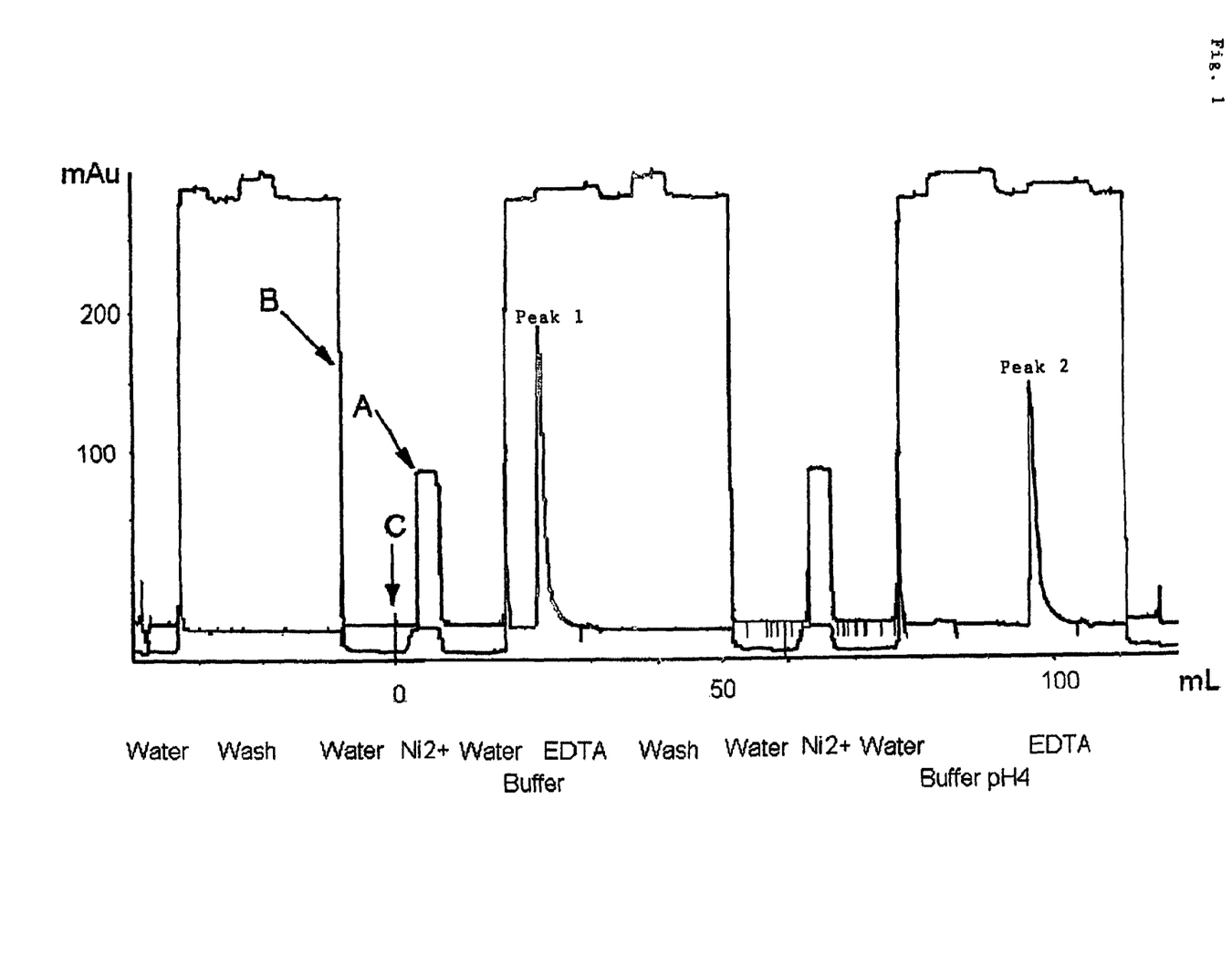
FIG. 1 shows a chromatogram of the nickel-binding capacity of a separation medium prepared according to the present invention and tested as described in the appended example 3.

FIG. 1 shows a chromatogram of the nickel-binding capacity of a separation medium prepared according to the present invention. The nickel binding capacity of the prototype separation medium synthesised according to Example 1 was determined to 22 μmol Ni/ml and the metal leakage to 16%, as described in example 3 below.

Figure 2:
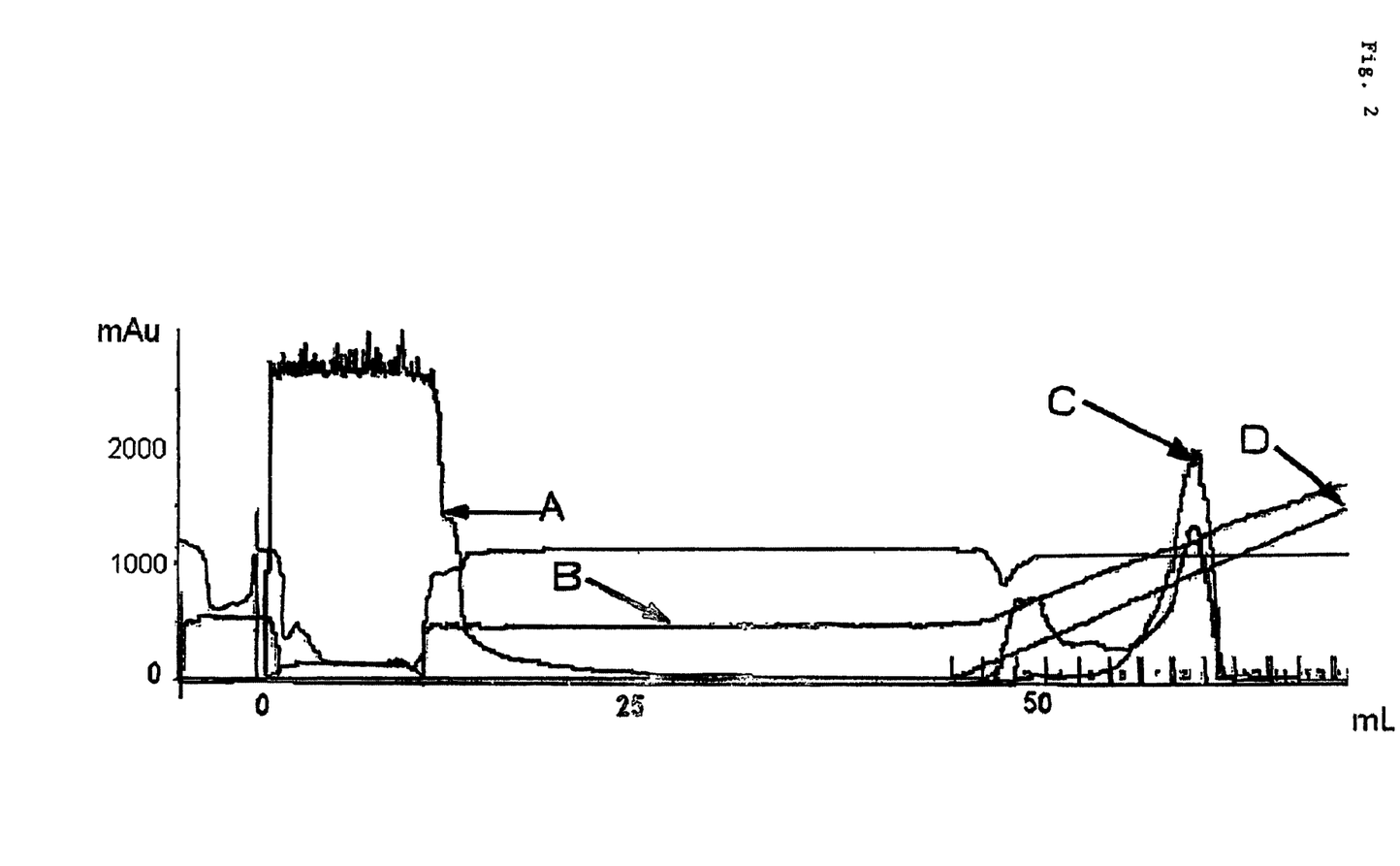
FIG. 2 shows a chromatogram illustrating the results of separation of His-tagged green fluorescent protein (GFP) as described in detail in example 4 below.

FIG. 2 shows a chromatogram illustrating the results of separation of His-tagged green fluorescent protein (GFP) as described in detail in example 4 below. In FIG. 2: A=A280 nm; B=A490 nm (absorbance of GFP-His); C=conductivity; and D=elution buffer (%). It appears from the chromatogram that UV absorbance at 490 nm, where essentially only GFP absorbs, is concentrated to one fraction, as illustrated by one peak.

EXPERIMENTAL PART

The present examples are provided for illustrative purposes only, and should not be construed as limiting the scope of the present invention as defined by the appended claims.

All references given below and elsewhere in the present specification are hereby included herein by reference.

The following abbreviations are used below:
DMF=N,N-Dimethylformamide
TLC=Thin layer chromatography
HOBt=1-Hydroxybezotriazole hydrate
NMR=Nuclear Magnetic Resonance
TMS=Trimethyl silane
EDC=N-(3-Dimethylaminopropyl)-N-ethylcarbodiimid hydrochloride
TFA=Trifluoroacetic acid
DCM=Dichloromethane
MO/Ce=1 g $Ce(SO_4)_2$ and 21 g $(NH_4)_6MO_7O_{24}$ $4H_2O$ in 31 mL $H_2SO_4$ diluted to 500 mL H₂O
DMSO=Dimethylsulfoxide
AGE=Allyl glycidyl ether
DCM=Dichloromethane
EDC=N-(3-dimethylaminopropyl)-N-ethylcarbodiimide hydrochloride

EXAMPLE 1

Synthesis of Prototype Ligand

For simplicity, the illustrative prototype ligand which was synthesised as described below is denoted "Ligand 41".

As regards the equipment used, $^1$H-NMR, $^{13}$C-NMR, CH-correlation, APT and cosy spectra were recorded in δ scale (ppm) with Bruker 300 MHz using TMS as reference. All spectra were recorded in CDCl₃ unless otherwise stated. TLC was carried out using Merck precoated silica gel $F_{254}$ plates. Ninhydrin or a mixture of MO/Ce was used to visualise spots on TLC plates. LC-MS data were recorded using Hewlett Packard 1100 MSD electrospray. The flash column chromatographic purifications were carried out using Merck G-60 silica gel.

Step (ii): Esterification of 2-amino-pentanedioic acid 5-tert-butyl ester 1-ethyl ester (41b)

A dry 250 mL round-bottomed flask was charged with 2.200 g (10.800 mmol) H-Glu(O-t-Bu)-OH (41a) dissolved in 100 mL ethanol. To this was added 4.4 g (22.9 mmol) EDC and 3.2 g (23.7 mmol) HOBt. The reaction mixture was stirred at ambient temperature for 22 h. The reaction mixture was followed to completion according to the LC-MS data. The solvent was removed under reduced pressure and the resulting oil was dissolved in dichloromethane 300 mL and extracted with H₂O 300 mL. The H₂O-phase was adjusted to pH 9.5. The crude product was extracted into dichloromethane 400 mL, dried over NaSO₄, filtrated and evaporated.

Yield:1.900 g (8.225 mmol), 75%. $^1$H-NMR (41b): δ 1.12–1.17 (t, 3H, CH₃—CH₂—O—), δ 1.40 (s, 9H, —O—C—(CH₃)₃), δ 1.78–2.01 (m, 2H, O═C—CH—CH₂—CH₂—C═O), δ 2.30–2.75 (m, 2H, O═C—CH—CH₂—CH₂—C═O), δ 2.27–2.30 (m, 2H, CH₃—CH₂—O—), δ 3.38 (m, 1H, O═C—CH—CH₂—CH₂—C═O); $^{13}$C-NMR (41b): δ 14.16 (CH₃—CH₂—O—), δ 24.90 (O═C—CH—CH₂—CH₂—C═O), δ 25.02 (O═C—CH—CH₂—CH₂—C═O), δ 27.88 (—O—C—(CH₃)₃), δ 53.90 (O═C—CH—CH₂—CH₂—C═O), δ 60.95 (CH₃—CH₂—O—), δ 79.82 (—O—C—(CH₃)₃), δ 169.12 (CH₃—CH₂—O—C═O), δ 179.38 (O═C—O—C—(CH₃)₃); LC-MS: M⁺ 232.

Step (iii): Derivatisation using bromo-acetic acid ethyl ester to provide 2-(ethoxycarbonylmethyl-amino)-penthanedioic acid 5-tert-butyl ester 1-ethyl ester (41c)

A dry 250 mL round-bottomed flask was charged with 1.200 g (5.195 mmol) (2-amino-pentanedioic acid 5-tert-butyl ester 1-ethyl ester (41b) dissolved in 50 mL DMF. To this was added 8.676 g (51.950 mmol, 5.76 mL) bromo-acetic acid ethyl ester, 862 mg (5.195 mmol) KI and 2.618 g (31.170 mmol) NaHCO₃. The reaction mixture was stirred at ambient temperature. The reaction was followed to completion (for 3.5 h) according to TLC (toluene:ethyl acetate 3:1) and LC-MS data. The product with $R_f$=0.39 was registered. The solvent was evaporated, the product was dissolved in CHCl₃, was washed with H₂O×2 and dried over Na₂SO₄, filtrated and evaporated. The titled compound was purified on flash column chromatography (toluene:ethyl acetate 3:1).

Yield: 2.000 g (4.963 mmol), 95%. $^1$H-NMR (41c): δ 1.20–1.22 (t, 6H, CH₃—CH₂—O—), δ 1.1.27–130 (t, 3H, CH₃—CH₂—O—), δ 1.43 (s, 9H, —O—C—(CH₃)₃), δ 1.90–2.01 (m, 2H, O═C—CH—CH₂—CH₂—C═O), δ 2.05–2.22 (m, 2H, O═C—CH—CH₂—CH₂—C═O), δ 3.10–3.47 (dd, 4H, O═C—CH₂—N—CH₂—C═O), δ 4.01 (t, 4H, CH₃—CH₂—O—), δ 4.40 (m, 1H, O═C—CH—CH₂—CH₂—C═O), δ 4.19–4.20 (t, 2H, CH₃—CH₂—O—); $^{13}$C-NMR (41c): δ 14.20 (CH₃—CH₂—O—), δ 27.01 (O═C—CH—CH₂—CH₂—C═O), δ 27.10 (O═C—CH—CH₂—CH₂—C═O), δ 27.92 (—O—C—(CH₃)₃), δ 52.10 (CH₃—CH₂—O—), δ 57.05 (O═C—CH₂—N—CH₂—C═O), δ 63.79 (O═C—CH—CH₂—CH₂—C═O), δ 80.17 (—O—C—(CH₃)₃), δ 172.24 (O═C—CH₂—N—CH₂—C═O), δ 176.57 (CH₃—CH₂—O—C═O), δ 181.57 (O═C—O—C—(CH₃)₃); LC-MS: M⁺ 404.

Step (iv): Selective cleavage of t-Bu ester to provide 2-(ethoxycarbonylmethyl-amino)-pentanedioic acid 1-ethyl ester (41d)

A dry 250 mL round-bottomed flask was charged with 2.00 g (4.963 mmol) 2-(ethoxycarbonylmethyl-amino)-penthanedioic acid 5-tert-butyl ester 1-ethyl ester (41c) dissolved in 50 mL DCM. To this was added 10 mL TFA. The reaction mixture was stirred at ambient temperature. The reaction was followed to completion (for 17 h) according to TLC (toluene:ethyl acetate 3:1) and LC-MS data. The solvent was evaporated, the product was dissolved in CHCl₃, was washed with H₂O×2 and dried over Na₂SO₄, filtrated and evaporated. The titled compound was purified on flash column chromatography (toluene:ethyl acetate 3:1).

Yield: 1.400 g (4.035 mmol), 81%. $^1$H-NMR (41d): δ 1.18–1.29 (t, 9H, CH₃—CH₂—O—), δ 2.13 (m, 2H, O═C—CH—CH₂—CH₂—C═O), δ 2.82 (m, 2H, O═C—CH—CH₂—CH₂—C═O), δ 3.36–3.47 (dd, 4H, O═C—CH₂—N—CH₂—C═O), δ 3.99–4.01 (t, 4H, CH₃—CH₂—O—), δ 4.40 (m, 1H, O═C—CH—CH₂—CH₂—C═O), δ 4.55 (t, 2H, CH₃—CH₂—O—); $^{13}$C-NMR (41d): δ 14.20 (CH₃—CH₂—O—), δ 27.01 (O═C—CH—CH₂—CH₂—C═O), δ 28.44 (O═C—CH—CH₂—CH₂—C═O), δ 52.10 (CH₃—CH₂—O—), δ 57.05 (O═C—CH₂—N—CH₂—C═O), δ 63.79 (O═C—CH—CH₂—CH₂—C═O), δ 63.77 (—O—CH₂—CH₃), δ 172.24 (O═C—CH₂—N—CH₂—C═O), δ 176.57 (CH₃—CH₂—O—C═O), δ 183.61 (O═C—O—H) LC-MS: M⁺ 347.

Results

The chemical structure of the prototype (ligand 41) is an analogue to the above discussed product disclosed in EP 87109892.7 (F. Hoffmann-La Roche AG), i.e. Ni—NTA, possessing the same chelating structure but with a different attachment point. According to the present invention, the attachment is performed via a carboxyl residue on the ligand, preferentially to a base matrix that possesses primary amines. The structure intended for coupling to the base matrix is protected on the three putative chelating carboxyl residues. This is necessary for obtaining selective coupling to the base matrix via the fourth (and unprotected) carboxyl residue. As a consequence of this, the ethyl ester protecting groups have to be hydrolysed after the ligand has been coupled to base matrix. This can be done by treatment with 1 M NaOH for three hours at 40° C. Hydrolysis conditions were first tested on the free ligand in solution, following the reaction with LC-MS, and eventually the completeness of the hydrolysis on base matrix was proven by solid phase $^1$H-NMR.

Ligand 41

In the scheme above, the schematic structure and synthetic route for Ligand 41 is shown.

During the development of the present route to produce Ligand 41, an alternative route starting from the commercially available methyl ester of glutamic acid was tried. This synthesis appeared to be attractive, since it was considerably shorter than the present route, but in that case it was not possible to cleave the methyl ester for the ligand in solution under conditions that should be acceptable for using with ligand attached to the base matrix (1 M NaOH or LiOH, elevated temperature for a prolonged period of time).

EXAMPLE 2

Immobilisation of the Prototype Ligand to a Base Matrix

In this example, ligand 41d was immobilised on monoamine gel prepared from AGE-activated Sepharose™ HP (Amersham Biosciences, Uppsala, Sweden) treated with ammonia:

-continued

Activation of Base Matrix

Allyl Activation with Allyl Glycidyl Ether (AGE) 200 ml drained Sepharose™ HP (Amersham Biosciences, Uppsala, Sweden) was slurried with 50 ml distilled water in a round-bottomed flask equipped with a mechanic stirrer. To this 2.6 g sodium hydroxide and 0.25 g $NaBH_4$ were added together with 12 g $Na_2SO_4$. The slurry was stirred at 50° C. for 1 h. To the reaction mixture allyl glycidyl ether (80 ml) was added and then stirring was continued at 50° C. for 16–18 h.

The gel was then filtered on a glass filter and washed thoroughly with distilled water, ethanol, distilled water, 0.2 M HOAc, and distilled water.

The allyl content was measured on a cube-ml gel with a titration method. The allyl content was determined to 40 μmol/ml gel.

Amine Activation with Ammonia (Monoamine X Gel) 30 ml drained Sepharose™ HP (Amersham Biosciences, Uppsala, Sweden) (43 μmol allyl/ml gel batch No. 513036), which had been allyl activated as described above, was suspended with 30 ml distilled water in a round bottomed flask equipped with a mechanic stirrer. Sodium acetate (2 g) was added to the slurry and the mixture was stirred at room temperature for 5 min. To this bromine water was added until a permanent yellow colour was obtained and then stirred for a further 5 minutes. The excess of bromine was destructed with Na-formiate. The gel was then filtered on a glass filter and washed thoroughly with water.

The allyl brominated gel was transferred into a round-bottomed flask equipped with a mechanic stirrer and to this ammonia (30 ml (25%)) was added. The mixture was stirred at 50° C. for 22 h. The gel was filtered and washed thoroughly with water, 0.5 M HCl, and 1 mM HCl. The Cl⁻ content was determined with a standard titration method.

Step (v): Immobilisation of Ligand to the Base Matrix

The above described amine activated base matrix was used in the immobilisation of the prototype ligand, which contains a carboxylic group (—COOH) as attachment point.

Ligand Activation

Ligand solution: 80 mg ligand 41d, 2.5 equivalent of the amine content (0.28 mmol), was dissolved in 2.5 ml DMF. To the solution 0.28 mmol DIPEA and 0.28 mmol EDC was added. The solution was stirred at room temperature for 15–20 minutes.

Coupling of the Ligand

The activated monoamine X gel (3 ml (37 μmol/ml gel)) was washed with 0.1 M NaOH, water and then with DMF. The gel was transferred to a tube with lid and to this the ligand solution was added. The reaction mixture was kept at room temperature for 16–18 h with shaking. The gel was filtered on a glass filter and washed with DMF.

The coupled ligand was washed on a glass filter with a 1:1 mixture of acetic anhydride:DMF. The gel was kept in the mixture 1:1 acetic anhydride:DMF at room temperature for 2 h and then filtered followed by washing with DMF, water and 1 M NaOH.

Deprotecting of the Ester Groups

The gel was transferred to a 20 ml scint. tube with lid and to this 8 ml, 1 M NaOH was added. The mixture was kept at 40° C. for 4 h. The gel was washed on a glass filter with water and then stored in 20% EtOH. The deprotecting of the ester groups (—COO—$CH_2$—$CH_3$) was analysed with HR-MAS.

Analysis

Investigation of the Deprotecting Reaction Time

Investigation of the deprotecting reaction times was performed using 5 ml base matrix with Ligand 41d coupled that was treated with 1 M NaOH and taking out samples after regular intervals. The efficiency of the deprotection of the ester groups was evaluated with HR-MAS.

Chromatographic Evaluation

IMAC separation medium prepared as described above comprising coupled ligand 41 was packed in a 1 ml HR 5/5 (Amersham Biosciences, Uppsala, Sweden) column that was mounted on an ÄKTA™ Explorer 10S system (Amersham Biosciences, Uppsala, Sweden). Evaluation of Ni-capacity and Ni-leakage (example 3) as well as frontal analysis and selectivity evaluation of his-tagged protein (example 4) were performed.

EXAMPLE 3

Determination of Metal-Binding Capacity and Metal-Leakage

Nickel-Binding Capacity

The nickel ($Ni^{2+}$) binding capacity of a separation medium prepared as described above was determined chromatographically using an ÄKTA™ Explorer 10 system (Amersham Biosciences, Uppsala, Sweden) equipped with a UV/Vis DAD detector. The test was performed on gel, to which Ligand 41 had been coupled according to the earlier description and which had been packed in 1-ml HR5/5 columns (Amersham Biosciences, Uppsala, Sweden).

More specifically, a $NiSO_4$ solution was injected to load the gel with $Ni^{2+}$ ions. Excess metal was removed by washing with water and phosphate buffer (20 mM $PO_4$, 500 mM NaCl, pH 7.4). The nickel ions bound to the gel were eluted with EDTA, which is a very strong chelator and efficiently strips the metal ions from the gel. The peak area of the green coloured Ni-EDTA complex eluted was measured at 372 nm. A linear calibration curve was established from solutions with different concentrations of Ni-EDTA and was used for quantification. The nickel-binding capacity (FIG. 1, peak 1) was given as μmol Ni/ml packed gel.

Metal Leakage

A metal leakage test was performed to test the stability of the ligand-nickel complex. The nickel-loaded gel was then washed with acetate buffer, pH 4.0. before determining the Ni content on the gel (FIG. 1).

For the present prototype, the metal leakage was determined to 16%.

Leakage of nickel ions was tested analogously to the above described nickel-binding capacity. However, before eluting nickel ions with EDTA, the gel was washed with ten column volumes of acetate buffer, 100 mM, pH 4.0. The leakage was given as % of the binding capacity and was determined as the difference between the nickel-binding capacity and the amount eluted after washing with pH 4, according to the formula: $(\text{area}_{Peak\ 2} - \text{area}_{Peak\ 1})/\text{area}_{Peak\ 1}$. (See FIG. 1)

EXAMPLE —4

Preparation of Sample for Chromatography (FIG. 2)

The *E. coli* extract with approximately 0.3 mg/ml of His-tagged Green Fluorescent Protein (GFP-His), 0.5 M NaCl, 5 mM imidazole and 1 mM PMSF (freshly added) was clarified by centrifugation and by 0.45 um filtration. The required volume was then introduced into a Superloop™ (Amersham Biosciences, Uppsala, Sweden) through a 0.2 um filter shortly prior to IMAC start. 9 ml was then applied to a Ni-loaded and equilibrated column packed with a 1-ml bed of Sepharose™ HP (Amersham Biosciences, Uppsala, Sweden) with ligand 41 as described above. (Ni-capacity=22.5 μmol/ml). After extensive washing with binding buffer, a 20-ml linear gradient was run (to 60% elution buffer=300 mM imidazole) using a chromatography system with a 10-mm UV-cell. Finally, a 5-ml push with 100% elution buffer (500 mM imidazole) was applied. All steps were at 1.0 ml/min.

What is claimed is:

1. A method of preparing a separation medium including a plurality of polydentate metal chelating affinity ligands immobilized to a base matrix, comprising the steps of:
    (i) providing a compound, having a terminal carboxyl group, of formula (I):

R—O—CO—(CH$_2$)$_n$—CHNH$_2$—CO—OH    (I), wherein
    R is a selectively cleavable group; and
    N is an integer from 1–4;
    (ii) reacting said compound with ethyl alcohol to provide esterification of the terminal carboxylic acid;
    (iii) derivatizing the reacted compound of step (ii) by adding at least one agent including an electrophile attached to an ethyl-protected carboxylic acid functionality;
    (iv) selectively cleaving R from the reacted compound of step (iii) to provide one free carboxylic acid functionality; and
    (v) immobilizing the compound that results from the step (iv) to a base matrix via said free carboxylic acid functionality, followed by deprotecting the remaining carboxylic acid groups by hydrolysis.

2. The method of claim 1, wherein R is t-butyl.

3. The method of claim 1, wherein the compound defined by formula (I) is ethyl ester of aspartic acid or ethyl ester of glutamic acid.

4. The method of claim 1, wherein the derivatization agent added in step (iii) is of the following formula (II):

E-(CH$_2$)$_m$—CO—O—CH$_2$—CH$_3$    (II), wherein E is an electrophile and m is an integer from 0–2.

5. The method of claim 1, wherein the matrix comprises primary amines.

6. The separation medium prepared by the method of claim 1.

7. The separation medium of claim 6, comprising tetradentate ligands.

8. The separation medium of claim 6, comprising tridentate ligands.

9. A chromatography column for immobilized metal ion adsorption chromatography (IMAC), packed with the separation medium of claim 6.

10. A kit for performing immobilized metal ion adsorption chromatography (IMAC), comprising the chromatography column of claim 9, metal ions for chelate formation and written instructions for its use.

11. A process of separating at least one target substance from a liquid, comprising charging the separation medium of claim 6 with metal ions to form chelates and contacting said medium with the liquid to adsorb the target substance(s), and further comprising the step of eluting the target substance(s) from the separation medium by adding a liquid that desorbs the target substance(s) from the separation medium.

12. A process of claim 11, wherein at least one target substance is membrane protein.

* * * * *